US006090093A

United States Patent [19]

Thibault et al.

[11] Patent Number: 6,090,093

[45] Date of Patent: *Jul. 18, 2000

[54] CONNECTOR ASSEMBLY FOR A VIAL HAVING A FLEXIBLE COLLAR

[75] Inventors: Jean Claude Thibault, Saint Egreve; Hubert Jansen, Poisat; Hervé Abry, Seyssins, all of France

[73] Assignee: Becton Dickinson and Company, Franklin Lakes, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/938,441

[22] Filed: Sep. 25, 1997

[51] Int. Cl.[7] .......................... A61B 19/00; B65D 39/00

[52] U.S. Cl. ......................... 604/415; 604/411; 215/253; 215/DIG. 3

[58] Field of Search ................................ 604/82, 86, 89, 604/91, 246, 249, 187, 415, 416; 222/145, 153, 129, 522, 525; 141/348, 349, 351; 251/325, 333, 344, 347, 349, 353

[56] References Cited

U.S. PATENT DOCUMENTS

| | | | |
|---|---|---|---|
| Re. 34,045 | 8/1992 | McFarland | 604/198 |
| 37,221 | 12/1862 | Dunton . | |
| 2,607,503 | 8/1952 | Sonnenberg | 215/38 |
| 2,667,986 | 2/1954 | Perelson | 215/48 |
| 2,953,132 | 9/1960 | Richter et al. | 128/272 |
| 3,164,303 | 1/1965 | Trautmann | 222/190 |
| 3,206,080 | 9/1965 | Scislowicz | 222/383 |
| 3,356,093 | 12/1967 | Monahon | 128/349 |
| 3,357,427 | 12/1967 | Wittke et al. | 128/235 |
| 3,674,028 | 7/1972 | Ogle | 128/272 |
| 3,779,371 | 12/1973 | Rovinski | 206/47 |
| 3,838,689 | 10/1974 | Cohen | 128/218 |
| 4,020,839 | 5/1977 | Klapp | 128/272 |
| 4,048,999 | 9/1977 | Köbel | 128/272.1 |
| 4,153,057 | 5/1979 | Köbel | 128/272.1 |
| 4,187,893 | 2/1980 | Bujan | 150/8 |
| 4,210,255 | 7/1980 | Pan | 220/209 |
| 4,336,891 | 6/1982 | Smith | 215/276 |
| 4,387,879 | 6/1983 | Tauschinski | 251/149.1 |
| 4,412,623 | 11/1983 | Schmidt | 215/11 R |
| 4,418,827 | 12/1983 | Butterfield | 215/247 |
| 4,425,120 | 1/1984 | Sampson et al. | 604/198 |
| 4,573,506 | 3/1986 | Paoletti | 141/98 |
| 4,573,976 | 3/1986 | Sampson et al. | 604/198 |
| 4,576,211 | 3/1986 | Valentini et al. | 141/329 |
| 4,672,996 | 6/1987 | Floyd et al. | 137/522 |
| 4,792,053 | 12/1988 | Towns et al. | 215/250 |
| 4,822,351 | 4/1989 | Purcell | 604/411 |
| 4,826,491 | 5/1989 | Schramm | 604/198 |
| 4,834,149 | 5/1989 | Fournier et al. | 141/1 |
| 4,834,152 | 5/1989 | Howson et al. | 141/286 |
| 4,850,994 | 7/1989 | Zerbst et al. | 604/198 |
| 4,884,703 | 12/1989 | O'Meara | 215/6 |
| 4,909,290 | 3/1990 | Coccia | 141/329 |
| 4,923,447 | 5/1990 | Morgan | 604/198 |
| 5,006,118 | 4/1991 | Yule | 604/408 |
| 5,088,996 | 2/1992 | Kopfer et al. | 604/415 |

(List continued on next page.)

FOREIGN PATENT DOCUMENTS 0 065 469 11/1982 European Pat. Off. .

(List continued on next page.)

*Primary Examiner*—Mark O. Polutta
*Assistant Examiner*—David J. Cho
*Attorney, Agent, or Firm*—Allen W. Wark

[57] ABSTRACT

A connector assembly for a vial is disclosed. The connector assembly features a protective cap, a collar attachable to the rim of the vial, and a crimp cap for securing the collar to the rim. The collar features a flexible skirt provided adjacent the proximal end of the collar that is foldable about the underside portion of the vial rim. One or more ribs are provided adjacent a distal portion of the collar to seal against the stopper obturating the vial. The crimp cap can be supplied preattached to the collar in an uncrimped condition. When crimped, the crimp cap exerts a force against the distal end of the collar and the flexible skirt folded about the rim to secure the collar to the vial. A vial access device is contained within the collar

10 Claims, 5 Drawing Sheets

U.S. PATENT DOCUMENTS

| | | | |
|---|---|---|---|
| 5,116,326 | 5/1992 | Schmidt | 604/198 |
| 5,171,214 | 12/1992 | Kolber et al. | 604/82 |
| 5,215,538 | 6/1993 | Larkin | 604/249 |
| 5,217,433 | 6/1993 | Bunin | 604/89 |
| 5,232,109 | 8/1993 | Tirrell et al. | 215/247 |
| 5,291,991 | 3/1994 | Meyer | 206/221 |
| 5,348,548 | 9/1994 | Meyer et al. | 604/403 |
| 5,352,196 | 10/1994 | Haber et al. | 604/90 |
| 5,358,501 | 10/1994 | Meyer | 604/414 |
| 5,360,413 | 11/1994 | Leason et al. | 604/249 |
| 5,385,546 | 1/1995 | Kriesel et al. | 604/85 |
| 5,423,791 | 6/1995 | Bartlett | 604/403 |
| 5,425,465 | 6/1995 | Healy | 215/355 |
| 5,429,256 | 7/1995 | Kestenbaum | 215/247 |
| 5,487,737 | 1/1996 | Meyer | 604/403 |
| 5,494,170 | 2/1996 | Burns | 215/247 |
| 5,520,661 | 5/1996 | Lal et al. | 604/246 |
| 5,533,983 | 7/1996 | Haining | 604/249 |
| 5,533,994 | 7/1996 | Meyer | 604/416 |
| 5,566,729 | 10/1996 | Grabenkort et al. | 141/25 |
| 5,598,939 | 2/1997 | Watson et al. | 215/307 |
| 5,613,291 | 3/1997 | Solomon et al. | 29/458 |
| 5,620,434 | 4/1997 | Brony | 604/406 |
| 5,662,230 | 9/1997 | Finneran | 215/252 |
| 5,685,845 | 11/1997 | Grimard | 604/82 |
| 5,702,019 | 12/1997 | Grimard | 215/301 |
| 5,803,284 | 9/1998 | Grimard | 215/249 |

FOREIGN PATENT DOCUMENTS

| | | |
|---|---|---|
| 0 263 127 A2 | 9/1987 | European Pat. Off. . |
| 0 406 374 B1 | 8/1993 | European Pat. Off. . |
| 1 487 413 | of 0000 | France . |
| 450 625 | 10/1949 | France . |
| 1 071 487 | 9/1954 | France . |
| 2738550 | 8/1997 | France . |
| 36 18 158 A1 | 12/1987 | Germany . |
| 2 738 550 | 9/1997 | Germany . |
| 501 172 | 2/1971 | Switzerland . |
| 659 519 | 10/1951 | United Kingdom . |
| 2 121 016 | 12/1983 | United Kingdom . |
| 95/03841 | 2/1995 | WIPO . |
| WO 95/03841 | 2/1995 | WIPO . |
| WO 97/39720 | 10/1997 | WIPO . |

CONNECTOR ASSEMBLY FOR A VIAL HAVING A FLEXIBLE COLLAR

FIELD OF THE INVENTION

The invention relates to a connector assembly for a vial, and more particularly, to a connector assembly for a vial which minimizes the number of components in the connector assembly and which reduces the number of microbial barriers necessary to safeguard sterility of the system.

BACKGROUND

In the art, it is generally known that to reduce inventory space or to increase the shelf life of certain drugs, or both, it is advantageous to reduce these drugs to a dry or powdered form. These dry or powdered drugs are normally stored in a sealed container such as a vial, and reconstituted into liquid form with an appropriate diluent or solvent solution prior to administration to a patient. The vials, typically formed of glass or plastic materials, include an elastomeric stopper sealing the open end of the vial. The stopper includes a portion inserted into the neck of the vial as well as a planar portion which rests on top of the vial, against the vial rim. The planar portion is normally tightly affixed to the vial rim with an aluminum crimp cap. Owing to the malleable nature of aluminum, the crimp cap readily adapts itself any differing dimension or tolerances which may exist between the stopper and the vial. The result is that the crimp cap evenly distributes sealing forces between the stopper and the vial. Thus, it has been generally recognized in the art that the vial/stopper/aluminum crimp cap solution safeguards the sterility of the drug contained within the vial over suitably long storage periods and prescribed conditions. The sizes and dimensions of the various vials and stopper components may be configured to given standards, such as given ISO standards.

One way to reconstitute the drug stored in the vial is to introduce the solvent or diluent from a syringe by piercing the stopper sealing the vial. Owing to various considerations, such as the convenience of the healthcare worker charged with reconstituting the drug, the art has recognized ways to transform the standard sealed vial into a system suitable for permitting safe, effective reconstitution of the drug contained within the vial. In these systems, typically, a fluid transfer assembly is connected to the neck of the vial. The fluid transfer system includes structure for connecting the vial to a source of diluent, such as diluent held in bottles, bags or syringes. The transfer assembly is thereafter activated to permit the flow of fluid into the vial to form the source of diluent, thereby reconstituting the drug.

In some configurations, the systems are such that standard vial stopper is eliminated in favor of fluid transfer assembly having a rubber stopper which is inserted into the neck of the vial, without the need for a planar portion which rests against the rim of the vial. This stopper remains within the neck until such time as reconstitution of the drug is desired. When the transfer assembly is activated, the stopper is urged towards the interior of the vial to open the neck, thereby permitting fluid to flow through the transfer assembly and into the vial body. Examples of such approaches include the MONOVIAL® line of drug delivery devices manufactured and sold by Becton Dickinson Pharmaceutical Systems of Le Pont de Claix, France and exemplified, for instance, by U.S. Pat. No. 5,358,501. While forming an excellent drug reconstitution system displaying superior properties, particularly convenience of use and sterility maintenance of the drug held in the vial, as typically configured these systems are useful for vial applications where the vial is of a relatively large size, typically 12 milliliters ("ml") or more. Accordingly, some pharmaceutical companies have expressed the desire for a reconstitution approach where the vial is of a size smaller than the sizes for which the aforementioned system is normally configured.

In response to the aforementioned concerns, then, one logical way around the dilemma would be to convert, as exactly as possible, the characteristics associated with vial components already in use by the pharmaceutical companies, such as ISO standard via/stopper/aluminum crimp cap components, and to implement a reconstitution system around these components for use by the healthcare worker. The prior art has considered some attempts in that regard. For instance, as exemplified by PCT Patent Application No. WO 97/10156 to Biodome, SA of Issoire Cedex, France, the aluminum crimp cap which would normally hermetically affix the planar portion of the standard stopper to the vial rim is replaced by a rubber-piercing fluid transfer assembly affixed around the neck of the vial. This rubber piercing fluid transfer assembly is activated by an end user when it is desired to reconstitute the drug held in the vial. The transfer assembly disclosed in this patent application features a fairly rigid, outermost plastic locking ring which, in theory, should lock the plastic transfer assembly firmly against the planar portion of the stopper and, hence, sealing this portion stopper against the vial rim. As has been pointed out, though, in practice, there may be significant variance between the dimensional tolerances of the glass components (the vial), the rubber components (the stopper) and the plastic components (the fluid transfer assembly) forming the system. The malleable nature of the aluminum crimp cap takes into account differences in tolerances. However, owing to the rigid characteristics of the sealing ring, with this approach, there may be the possibility that given a particular vial, stopper, or transfer assembly, the sealing forces realized by the outside sealing ring against the stopper and the vial may not be sufficient or otherwise uniform. Accordingly, the potential contamination of the drug, given the environmental stresses to which the vial may be subject to during manufacture, shipping, or storage, presents a concern.

Accordingly, there is a need for a safe and effective drug reconstitution system, wherein a fluid transfer assembly is affixed to a standard vial and stopper arrangement in a manner such that the sealing forces achievable by an aluminum crimp cap are effectively replicated. Such a drug reconstitution system is disclosed herein.

SUMMARY OF THE INVENTION

The present invention addresses the aforementioned concerns in a convenient and cost-efficient manner. A connector assembly in accordance with the present invention is designed to be employed with a standard vial and stopper so as to be able to be processed by a pharmaceutical manufacturer with standard processing equipment. The connector assembly is fully able to account for dimensional variances or tolerance variances in the vial or stopper components or in the components forming the connector assembly itself, so as to ensure good microbiological barrier characteristics.

The connector assembly features a protective cap for covering the open end of the vial neck. The cap includes an open proximal end, a closed distal end, and a shield wall formed therebetween. A collar is provided adjacent the open proximal end of the cap. The collar can be molded with the cap, or it can be separately manufactured and thereafter affixed to the cap. The collar features a proximal end, a distal end, and a sidewall therebetween. One or more rib elements are provided on an interior portion of the collar adjacent the distal end, and the ribs designed to form a tight seal against the stopper as the collar is positioned against the stopper. Interior portions of the collar can be configured to mate with a vial access device provided to pierce the stopper.

A defining aspect of the collar is the provision of a flexible skirt adjacent the proximal end of the collar. The skirt is foldable about the rim of the vial when the collar is positioned against the stopper so as to engage the underside portion of the rim. The skirt can be formed on the collar in a variety of ways.

A crimp cap fixes the collar to the vial rim. As the collar is locked to the rim of the vial by the crimp cap, the crimp cap exerts a force against the distal end of the collar and against the skirt that has been folded against the underside portion of the rim. The collar is thus tightly thrust against the stopper, thereby ensuring a proper seal of the stopper to the vial. Additionally, the ribs provided in the internal portion of the collar form an additional microbiological barrier against the ambient environment. The crimp cap can be preaffixed to the collar in an uncrimped condition, with the crimping operation occurring after the collar is placed around the vial rim. Alternately, the crimp cap can be affixed about the collar after the collar is placed onto the vial rim.

The connector assembly can be shipped to a pharmaceutical manufacturer, either with the crimp cap preaffixed or not. In the cleanroom environment where the vial is filled with a medicament and the stopper is placed against the rim, the connector assembly can be attached to the vial. The connector assembly is transferred from a first position, whereby the collar is placed around the rim and the distal end of the collar spaced from the stopper, to a second position, whereby the flexible skirt of the collar is projected beyond the underside portion of the rim. By this action also, the ribs provided in the interior of the collar are thrust into sealing relation with the stopper. Thereafter, the crimp cap is positioned in crimped relation about the collar and the vial rim to secure the collar the vial rim. The crimp cap will exert a force against the flexible skirt, folding it against the underside portion of the rim into secured relation with it. The flexibility imparted by the skirt allows the collar to compensate for any dimensional or tolerance variations present in the vial, the stopper, or in the connector assembly itself If the crimp cap is supplied to the customer pre-attached to the collar but in an uncrimped state, the connector assembly itself is secured to the vial in sealing relation with the stopper within the cleanroom environment, and the crimping operation itself need only occur outside of the cleanroom.

If desired, the cap and collar can be manufactured in such a manner such that the cap is removable from the collar by a twisting action, permitting a user a convenient way to engage the vial access device held by the connector assembly. In one configuration, the cap can be formed with the collar with a frangible connection formed from a material—such as a thermoplastic elastomer—that is different from the material forming the cap and collar itself, such as polypropylene or polyethylene. The user may simply twist the cap such that the frangible connection shears, allowing the user to remove the cap from the collar to expose the vial access device. One way to achieve this construction is through a co-injection process. All in all, the minimization of the number of components forming the connector assembly results in a concomitant reduction in the number of biological barriers necessary to safeguard the sterility of the vial access device as well as the medicament contained within the vial.

BRIEF DESCRIPTION OF THE DRAWINGS

The invention will now be described in detail by way of reference to the appended drawings, wherein.

DETAILED DESCRIPTION OF THE PREFERRED EMBODIMENTS

A convention used throughout this application is that the term "proximal" denotes a distance closest to rim 14 of vial 10, while the term "distal" denotes a distance furthest from the rim of the vial.

Figure 1:
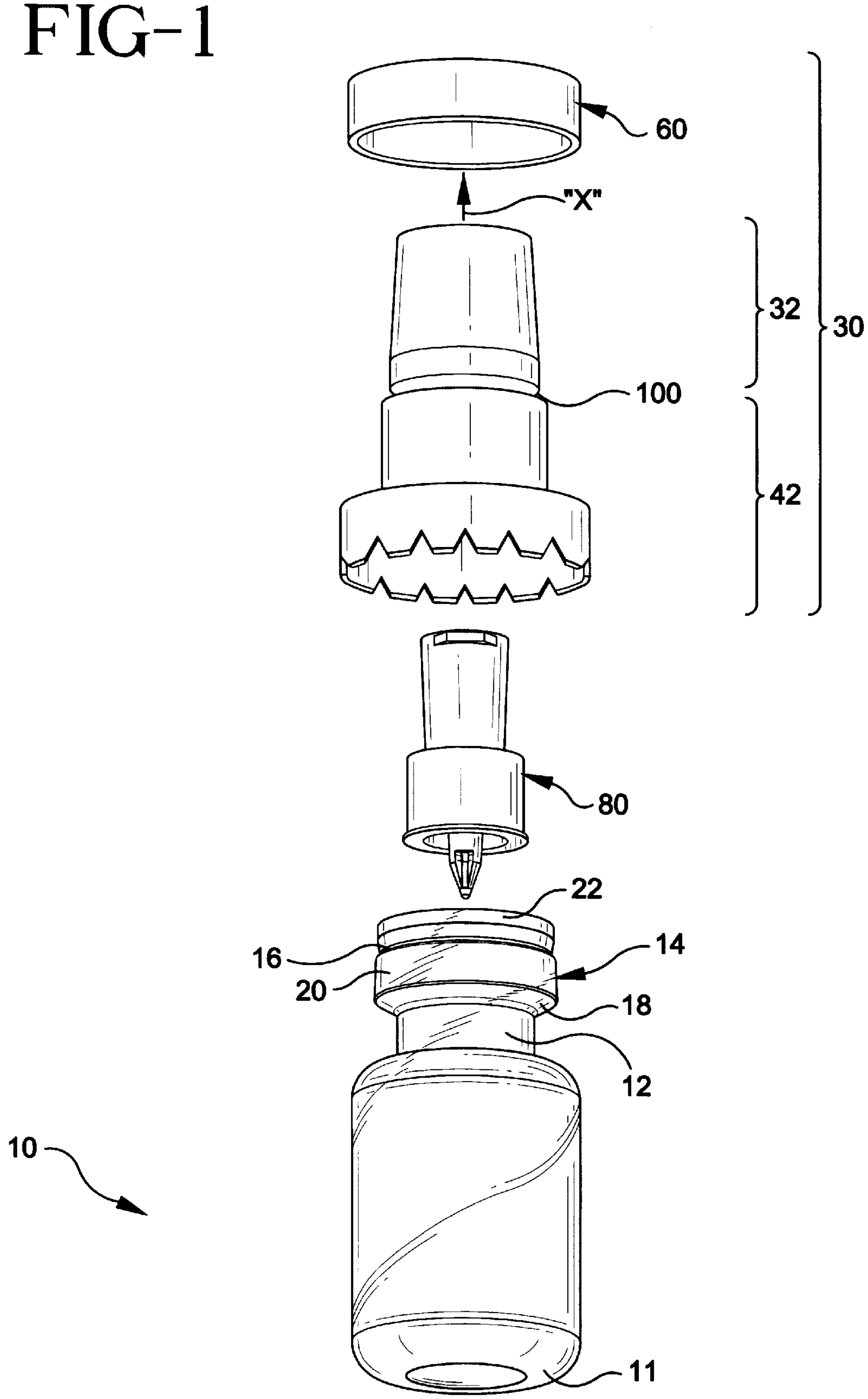
FIG. 1 is an exploded view of a first embodiment of the connector assembly in accordance with the present invention.
Figure 2:
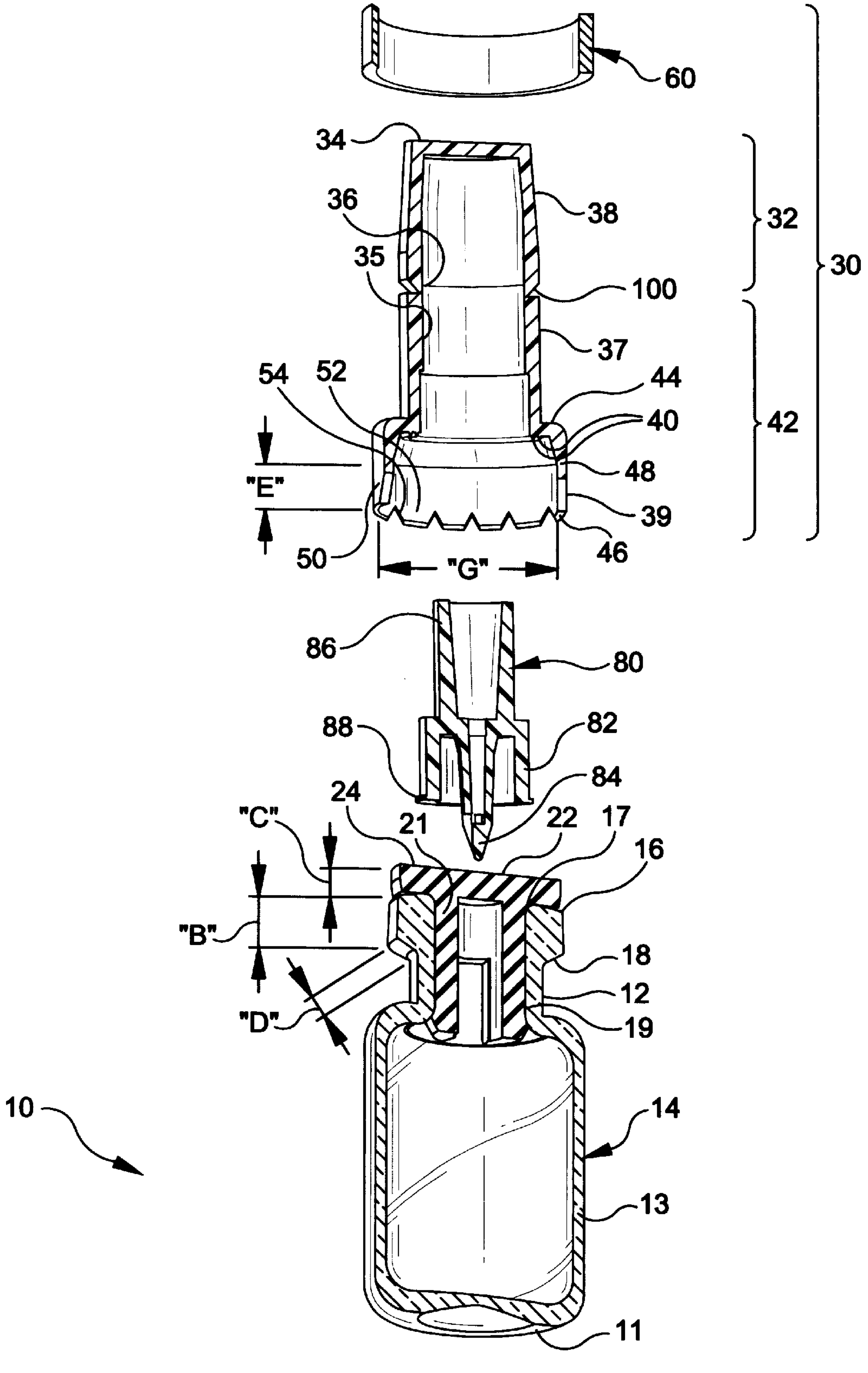
FIG. 2 is a cross-sectional view of FIG. 1.

Turning to the drawings, wherein like numerals denote like components, FIGS. 1 and 2 illustrate a first embodiment 30 of a connector assembly for a vial 10 in accordance with the present invention. Vial IO is characterized by a bottom wall 11, a sidewall 13, a neck 12 and an annular rim 14. Annular rim 14 includes an underside portion 18, a side portion 20, and a top surface 16. A stopper 22 is typically employed to obturate an open end 17 associated with the vial. Stopper 22 features a planar portion 24 covering top surface 16 of the rim, and a plug portion 21 obturating the inside surface 19 of neck 12. Vial 10 is typically filled with a desired medicament, such as a dry drug or a lyophilized drug, and thereafter affixed with stopper 22, in a cleanroom environment. For the purposes of this invention, it will be realized that the dimensions and characteristics of vial 10 and stopper 22 can be conformed to various accepted standards, such as ISO standards, governing vials and stoppers intended for medicamental use.

As previously explained, a drawback in the art is ensuring that proper sealing forces exist between stopper 22 and vial 10. It would also be advantageous to incorporate a solution to this problem in a vial connector assembly that is easily processed by the pharmaceutical manufacturer and which, desirably, can be fully processed in the cleanroom environment where medicaments are processed, introduced into the vial, and stoppered within the vial.

With the foregoing in mind then, a first embodiment 30 of the connector assembly of the present invention is provided. Connector assembly 30 is formed of three principal components, namely, a cap 32, a collar 42, and a crimp cap 60.

Cap 32 is characterized by a closed distal end 34, an open proximal end 36, and a shield wall 38 therebetween. Cap 32 is provided adjacent collar 42. Cap 32 and collar 42 can be formed together, such as by a co-injection process, or they can be separately formed and joined together by mechanical means, welding, or the like. In a preferred construction, cap 32 and collar 42 are formed together and connected by a frangible section 100, as will be hereinafter discussed.

Collar 42 is designed to mate with rim 14 of the vial. Collar 42 is located adjacent open proximal end 36. Collar 42 includes an upstanding tubular section 37 defining an interior portion 35. Interior portion 35 serves to engage a vial access device, as will be more fully explained hereinbelow. Adjacent tubular section 37 there is provided a vial attachment section 39. Vial attachment section 39 of the collar displays a distal end 44, an open proximal end 46, and a sidewall 48 therebetween. One or more sealing ribs 40 are provided, on an interior portion of vial attachment section 39, adjacent distal end 44. Ribs 40 can take any shape appropriate to their sealing function, such as rounded, peaked, square, or other geometries.

Figure 4:
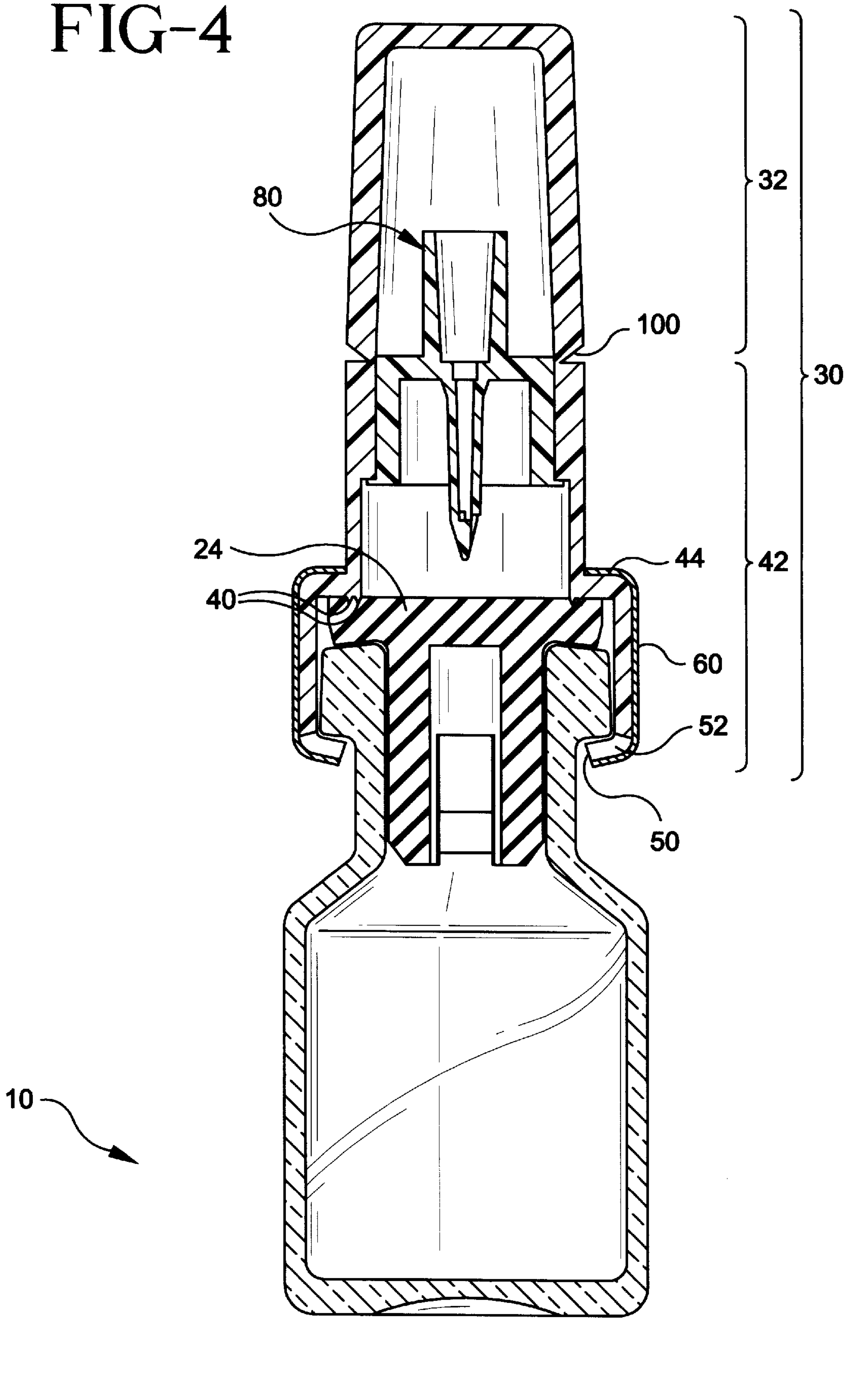
FIG. 4 is a cross-sectional view depicting the crimp cap applied to the connector assembly such that the skirt is folded against the underside portion of the rim.

A distinguishing feature of the collar is its ability to compensate for dimensional or tolerance variances between the stopper, the vial, or the connector assembly itself, so as to ensure that uniform sealing forces are applied over the surface of stopper 22. To this end, collar 42 is formed with a flexible skirt 50 provided adjacent proximal end 46 of the collar. Flexible skirt 50 is designed to fold about and engage underside portion 18 of the rim when the connector assembly is locked to vial in the second position (FIG. 4). Flexible skirt 50 displays a length "E" preferably equal to, if not slightly less than, a width "D" displayed by underside portion 18 of the rim (FIG. 2).

Flexible skirt 50 can be provided to collar 42 in a variety of ways. For instance, as depicted, flexible skirt 50 can be formed by providing a plurality of cutouts 54 about the proximal end 46 of the collar. The effect of the cutouts is to create a plurality of teeth 52 about the proximal end of collar 42 that, owing to the cutouts, are flexible about the underside portion of rim 14. In lieu of cutouts, a plurality of slits (not shown) can also be provided in sidewall 48 in the area of skirt 50, each of those slits emanating from proximal end 46 of the collar. The effect of the slits is to allow the sidewall, in the region of skirt 50, to flex about underside portion 18 of the rim. Another way to form skirt 50 may be created is by thinning the corresponding section of sidewall 48, in the region of skirt 50, to an appreciable degree with respect to the reminder of sidewall 48. The effect of thinning the sidewall in the area of the skirt is to impart flexibility, allowing the skirt to fold about the underside portion of rim 14. Other manners of forming the skirt will be appreciated and within the realm of the skilled artisan.

The effect of skirt 50 is to impart a degree of elasticity or flexibility to collar 42, allowing it to account for dimensional or tolerance variances in the various components. For instance, the existence of skirt 50 imparts a degree of flexibility to vial attachment section 39 of the collar in an axial direction parallel to central axis X of cap 32. Thus, if for some reason the thickness "C" of planar portion 24 of the stopper or the thickness "BB" of side portion 20 of the rim (FIG. 2) is not uniform, the folding property of the vial attachment section of collar 42 allows collar 42 to respond in an axial direction to account for those variances. It is important to note, too, that the hardness displayed by the materials forming either of stopper 22 or vial 10 may affect the ultimate combined thicknesses "B" and "C" of the rim and stopper and, thus, the sealing force ultimately exerted by ribs 40 against the stopper. Thus, the provision of skirt 50 helps to compensate for such variances as well. All in all, then, the sealing force imparted by ribs 40 will be constant from one connector assembly 30 to another.

Inside diameter "G" of vial attachment section 39 should be chosen such that it is at least equal to, or slightly less than, outside diameter "F" of rim 14 (FIG. 3) when the collar is in an unflexed condition. By unflexed condition, what is meant is that skirt 50 is not compressed or expanded axially or radially from its original configuration on collar 42.

Crimp cap 60 is disposed about collar 42. Crimp cap 60 is preferably of the conventional aluminum type which, when a crimping operation is applied, exerts a force against distal end 44 and skirt 50, causing skirt 50 to fold about underside portion 18 of the rim, and locking the collar to the vial rim (FIG. 4). If desired, the connector assembly can be supplied with crimp cap 60 pre-attached to collar 42 in an uncrimped condition, such that connector assembly 30 together with the uncrimped crimp cap 60 are applied to the vial in the cleanroom, and the ribs 40 urged into sealing relation with stopper 22. Thus, the only operation which need occur outside of the cleanroom is the actual crimping operation. Crimp cap 60 thus serves to lock the collar to the rim in the second position.

Connector assembly 30 typically encloses a vial access device 80. Vial access device 80 is structured to pierce stopper 22 so as to gain access to the medicament held by vial 10. While not limited in scope, in general vial access device 80 may feature a body 82 in frictional engagement with an interior surface 35 associated with tubular section 37 of the collar. A distally facing piercing element 84 is mounted to the body. A connector end 86, attached in fluid communication to piercing element 84, is provided to mount the vial access device to an external component such as a syringe, a rigid bottle, a flexible bottle, or the like. It will be realized by the skilled artisan that piercing element 84 can take various configurations, such as a pointed metallic or plastic needle, a spike, or any pointed structure serving to pierce stopper 22. Similarly, connector end 86 can be configured as a spike, a needle, as a luer connector, or any other desirable configuration to mate with the various external components, such as rigid fluid bottles, luer lock or luer slip syringes, flexible fluid bags, or the like, with which an end user will want to employ with the connector assembly.

Operation of the connector assembly will now be explained, referring principally to FIGS. 3 and 4.

In practice, the pharmaceutical customer would process or otherwise fill a desired medicament in vial 10, thereafter applying stopper 22 to the vial neck. Both of these operations would occur in a cleanroom environment. As illustrated in FIG. 3, the component manufacturer would normally supply connector assembly 30 to the pharmaceutical manufacturer in a pre-assembled sterile state, ready to apply to an already stoppered vial.

Figure 3:
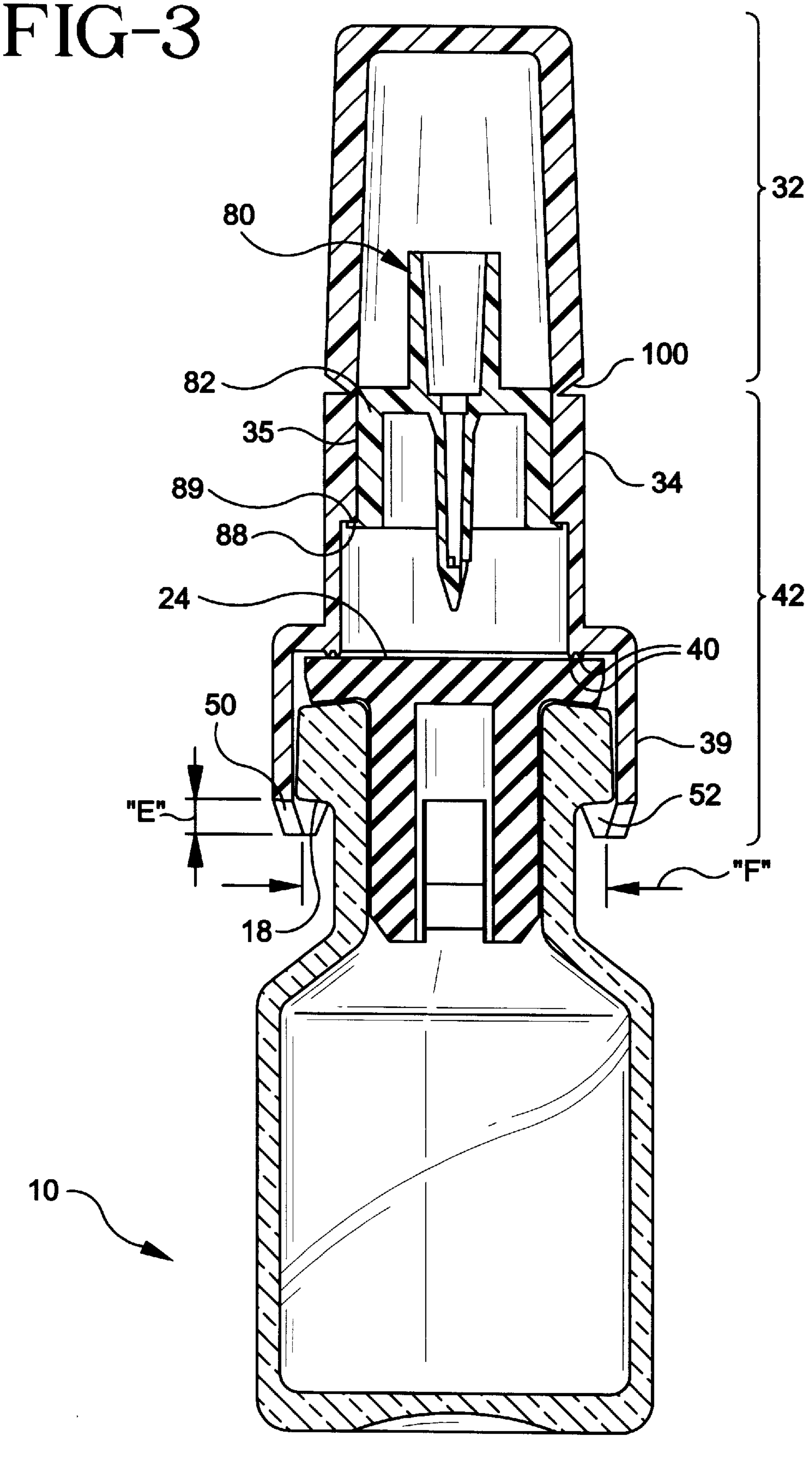
FIG. 3 is a cross-sectional view depicting placement of the connector assembly against the vial in a first position, wherein the collar is placed around the rim and the flexible skirt urged beyond the underside portion of the rim.

As illustrated in FIG. 3, in the pre-assembled state, collar 42 is positioned such that skirt 50 is in an unfolded position respective of the collar. That is to say, skirt 50 is substantially co-planar with sidewall 48 of the collar. Pre-assembled connector assembly 30 is thus placed over vial 10 directly in the cleanroom, with proximal end 46 of the collar passing around rim 14, and skirt 50 positioned in an area beneath underside portion 18 of the rim. As the collar is displaced against stopper 22, the folding property of the skirt permits it to accommodate any dimensional or tolerance variances, as previously described. This property contributes to ensuring that equal forces will be exerted by the collar across the surface of the stopper, ensuring a proper seal between the stopper and the vial. It will also be seen that ribs 40 are placed against planar portion 24 of the stopper into sealing contact at this time. The ribs will bite into stopper 22, creating a microbiological barrier serving to isolate vial access device 80 contained inside cap 32 and collar 42. While not illustrated, various detent mechanisms, such as ribs, can be provided on an interior portion of collar 42 to engage the rim, thereby retaining the collar against the stopper with the ribs in sealing contact.

Once the connector assembly has been urged such that a seal has been formed between ribs 40 and planar portion 24 of the stopper, the connector assembly and vial can be removed from the cleanroom environment for the final assembly step, represented by FIG. 4. In FIG. 4, crimp cap 60 has been applied about collar 42. Crimp cap 60 exerts a force both against distal end 44 and against skirt 50 of the collar, in effect squeezing the distal end and the skirt towards one another. The crimp cap will thus fold sunderside portion underside portion 18 of the rim. The squeezing act bite tightly into planar portion 24 of the stopper, thereby ensuring a good microbiological seal between the ribs and the stopper. At the same time, stopper 22 is also pressed into good sealing contact with rim 14, ensuring a good microbiological seal between the two. The effect is that two microbiological barriers are created—one between the sealing ribs and the planar portion of the stopper, and one between the planar portion of the stopper and upper surface 16 of the rim—in an unformed manner across the entire planar portion of the stopper. Vial access device 80 is thus secured in microbiological isolation within connector assembly 30, and stopper 22 tightly sealed to vial 10 so as to isolate the drug held by the vial. Connector assembly 30 is now securely affixed to the vial, and the pharmaceutical manufacturer may ship the filled vial to the end user.

Figure 5A:
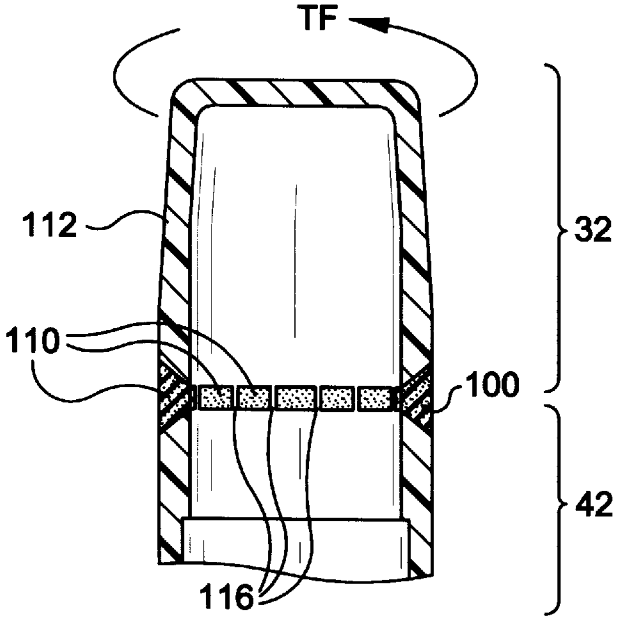
FIGS. 5A and 5B depict two manners of configuring a frangible section between the cap and the collar to permit removal of the cap from the collar to expose the vial access device.
Figure 5B:
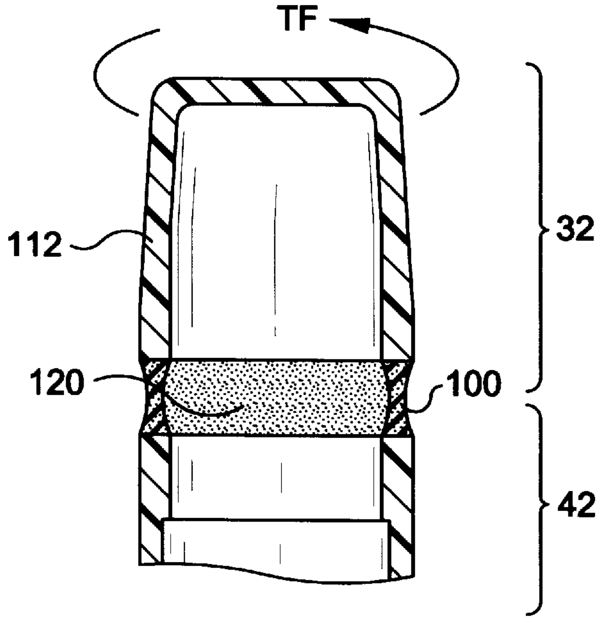

To employ the vial, cap 32 is removed from collar 42 so as to expose vial access device 80. While various ways can be configured to so remove the cap, FIGS. 5A and 5B illustrate forming cap 32 and collar 42 together and connecting them by a frangible section 100. Frangible section 100 permits a user to apply a twisting force to cap 32 so as to remove the cap from the collar to expose vial access device 80. Cap 32 and collar 42 may be formed together by a co-injection process, wherein a material having a low shear resistance is employed for frangible section 100, and a material having a higher shear resistance is employed for the rest of the cap and the collar. For instance, frangible section 100 can be formed by employing various thermoplastic elastomers ("TPE") displaying low shear resistance, and which display good adhesion properties to the material chosen for the rest of the cap, which typically can be polypropylene or polyethylene.

As illustrated in FIG. 5A, frangible section 100 can be configured as a series of TPE pockets, or "teeth", 110 that are molded into an interior section 112 defined between cap 32 and collar 42. Teeth 110 are interspersed with intervening portions 116 of frangible section 100, the intervening portions formed from the more shear resistant material that makes up the remainder of cap 32 or collar 42. The resulting frangible section 100 allows a user to exert a moderate twisting force "TF" against the cap to remove it. At the same time, the presence of intervening sections 116 strengthen the frangible section against inadvertent removal of the cap caused, for instance, by jostling during shipment, inadvertent opening by an end user, or the like. Alternately, as illustrated in FIG. 5B, if desired, frangible section 100 can be formed as a solid section 120 of TPE material across interior section 112. In any event, by forming cap 32 and collar 42 as a single unit, an additional, potential area for microbiological contamination—the juncture between the cap and the collar—is eliminated, leading to a concomitant reduction in the number of microbiological barriers needed.

It will also be realized that cap 32 and collar 42 can be formed separately and attached by various means, such as by welding, adhesives, or the like. That will safeguard integrity of the connection between the cap and the collar, but that will provide a reasonable force to permit a user to remove the cap.

In use then, cap 32 is removed from collar 42, and vial access device 80 exposed. An external component (not shown) is attached to connector end 86, and a proximally directed force applied. Piercing element 84 is urged through stopper 22 and in communication with the interior of the vial. Body 82 is slidably disposed with respect to interior surface 35 of shield wall 38. The engagement between body 82 and interior surface 35 can be by frictional engagement, via mechanical engagement such as by threaded engagement or by a lot and follower arrangement, or by other arrangements within the realm of the skilled artisan. If desired, body 82 can be retained against inadvertent removal from shield wall 38 by providing a stop 88 adjacent a proximal end of body 82 that is arrested by a shoulder 89 inside shield wall 38.

The various components can be constructed from materials standard in the art. For example, the cap, the collar, and the ring can be injection molded from various thermoplastics (the construction of the frangible section having been already explained). The vial access device can be made from various medical grade plastics, medical grade stainless steels, combinations of these materials, or the like. Various rubbers or elastomers can be chosen for the stopper, and the vial can be made from suitable glass or plastics materials adapted to the drug held therein. If desired, various tamper evidence means, such as heat shrunk plastic strips, can be incorporated between the vial and the collar.

It will be appreciated and understood by those skilled in the art that further and additional forms of the invention may be devised without departing from the spirit and scope of the appended claims, the invention not being limited to the specific embodiments shown.

We claim:

1. A connector assembly for a vial, said vial including a neck, an open end at the proximal end of the neck, a rim bounding the open end, and a stopper obturating the open end of the vial, the rim having a side portion and an underside facing away from the open proximal end of the vial, the stopper having a planar portion covering the rim, the connector assembly comprising:

a vial access device; and a protective cap for covering the open end of the vial, the cap comprising an open proximal end, a closed distal end, and a shield wall formed therebetween, said protective cap having a frangible section situated along the shield wall between the open proximal end and the closed distal end, said frangible section including a first material and at least partially including a second material having a low shear resistance; and said frangible section including a plurality of teeth formed from said second material interspersed with intervening portions of said frangible section and said intervening portions being formed from said first material having a more shear resistance material and making the remainder of the protective cap so that said intervening sections strengthen the frangible section against inadvertent removal of the protective cap and so that at least a portion of said protective cap may be removed from said vial by applying a twisting force to said protective cap to expose said vial access device.

2. The connector assembly of claim 1, wherein said second material having a low shear resistance fills said teeth.

3. The connector assembly of claim 2, wherein said second material having a low shear resistant is a thermoplastic elastomer co-injected with said first material having a more shear resistance to form said protective cap.

4. The connector assembly of claim 3, wherein said first material having a more shear resistance is selected from the group consisting of polypropylene or polyethylene.

5. The connector assembly of claim 1, wherein said protective cap includes a cap portion and a collar portion formed together and connected by said frangible section situated along the circumference of said protective cap.

6. A connector assembly for a vial, said vial including a neck, an open end at the proximal end of the neck, a rim bounding the open end, and a stopper obturating the open end of the vial, the rim having a side portion and an underside facing away from the open proximal end of the vial, the stopper having a planar portion covering the rim, the connector assembly comprising:

a vial access device; and a protective cap for covering the open end of the vial, the cap comprising an open proximal end, a closed distal end, and a shield wall formed therebetween, said protective cap having a frangible section situated along the shield wall between the open proximal end and the closed distal end, said frangible section including a first material and at least partially including a second material having a low shear resistance co-injected with said first material so that at least a portion of said protective cap my be removed from said vial by applying a twisting force to said protective cap to expose said vial access device.

7. The connector assembly of claim 6, wherein said frangible section includes a plurality of teeth formed from said second material interspersed with intervening portions of said frangible section and said intervening portions being formed from said first material having a more shear resistance material and making up the remainder of the protective cap so that said intervening sections strengthen the frangible section against inadvertent removal of the protective cap.

8. The connector assembly of claim 7, wherein said second material having a low shear resistance fills said teeth.

9. The connector assembly of claim 8, wherein said second material having a low shear resistant is a thermoplastic elastomer and said first material having a more shear resistance is selected from the group consisting of polypropylene or polyethylene.

10. The connector assembly of claim 6, wherein said protective cap includes a cap portion and a collar portion formed together and connected by said frangible section situated along the circumference of said protective cap.

* * * * *